United States Patent [19]
Heil et al.

[11] Patent Number: 5,942,528
[45] Date of Patent: Aug. 24, 1999

[54] ACYLATED 5-AMINO-1,2,4-THIADIAZOLES AS PESTICIDES AND FUNGICIDES

[75] Inventors: Markus Heil, Leverkusen; Christoph Erdelen, Leichlingen; Ulrike Wachendorff-Neumann, Neuwied; Andreas Turberg, Haan; Norbert Mencke; Gerd Hänssler, both of Leverkusen; Klaus Stenzel, Düsseldorf, all of Germany

[73] Assignee: Bayer Aktiengesellschaft, Leverkusen, Germany

[21] Appl. No.: 09/101,116

[22] PCT Filed: Jan. 3, 1997

[86] PCT No.: PCT/EP97/00012

§ 371 Date: Jun. 30, 1998

§ 102(e) Date: Jun. 30, 1998

[87] PCT Pub. No.: WO97/26251

PCT Pub. Date: Jul. 24, 1997

[30]  Foreign Application Priority Data

Jan. 15, 1996 [DE] Germany .............. 196 01 139

[51] Int. Cl.⁶ .............. C07D 285/08; A01N 43/82
[52] U.S. Cl. .............. 514/361; 548/128
[58] Field of Search .............. 548/128; 514/361

[56]  References Cited

U.S. PATENT DOCUMENTS 5,705,650  1/1998  Tatsuta ..................... 548/128

FOREIGN PATENT DOCUMENTS

| 378 308 | 7/1990 | European Pat. Off. . |
| 389 901 | 10/1990 | European Pat. Off. . |
| 632 282 | 11/1994 | European Pat. Off. . |
| 3 505 432 | 8/1986 | Germany . |

*Primary Examiner*—Robert Gerstl
*Attorney, Agent, or Firm*—Sprung Kramer Schaefer & Briscoe

[57]  ABSTRACT

The present invention relates to novel acylated 5-amino-1,2,4-thiadiazoles of the formula (I)

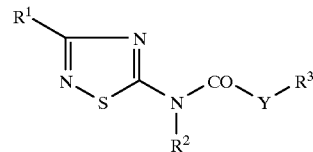

in which $R^1$, $R^2$, $R^3$ and Y each have the meanings stated in the description, a process for their preparation, and to their use for controlling animal pests.

9 Claims, No Drawings

ACYLATED 5-AMINO-1,2,4-THIADIAZOLES AS PESTICIDES AND FUNGICIDES

The present invention relates to novel acylated 5-amino-1,2,4-thiadiazoles, a process for their preparation, and to their use for controlling animal pests and as fungicides.

It is already known that certain acylated 4-cyano-5-aminoisothiazoles have insecticidal properties (cf. for example EP-A-0 623 282).

However, the potency and persistency of these prior-art compounds is not always entirely satisfactory, in particular at low application rates and concentrations.

The invention provides novel acylated 5-amino-1,2,4-thiadiazoles of the formula (I)

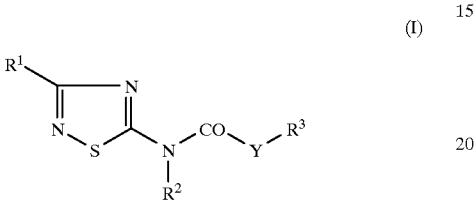

in which
$R^1$ represents alkyl, halogenoalkyl, alkoxyalkyl, alkylthioalkyl, alkoxy, alkylthio or optionally substituted cycloalkyl,
$R^2$ represents hydrogen, alkyl, halogenoalkyl, alkoxyalkyl, alkylcarbonyl, alkylsulphonyl, respectively optionally substituted arylcarbonyl, arylsulphonyl or arylalkyl or optionally substituted cycloalkyl,
$R^3$ represents optionally substituted aryl, optionally substituted cycloalkyl or optionally substituted cycloalkenyl and
Y represents optionally substituted alkylene, alkenylene or alkyleneoxy.

Furthermore, it has been found that the acylated 5-amino-1,2,4-thiadiazoles of the formula (I) are obtained when 5-amino-1,2,4-thiadiazoles of the formula (II)

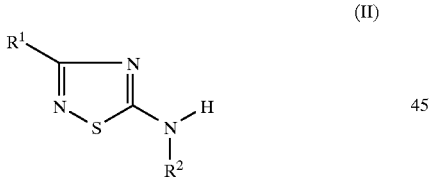

in which
$R^1$ and $R^2$ each have the meanings stated above are reacted with acid halides of the formula (III)

in which
$R^3$ and Y each have the meanings stated above and
Hal represents halogen
in the presence of a base and in the presence of a diluent.

Finally, it has been found that the novel acylated 5-amino-1,2,4-thiadiazoles of the formula (I) have pronounced biological properties and are especially suitable as fungicides and for controlling animal pests, in particular insects, arachnids and nematodes encountered in agriculture, in forestry, in the protection of stored products and materials, and in the hygiene sector.

Formula (I) provides a general definition of the acylated 5-amino-1,2,4-thiadiazoles according to the invention.

Preferred substituents or ranges of the radicals mentioned in the formulae given hereinabove and hereinbelow will now be illustrated.

$R^1$ preferably represents $C_1$–$C_4$-alkyl, $C_1$–$C_4$-halogenoalkyl having 1 to 5 identical or different halogen atoms, such as fluorine, chlorine and bromine atoms, $C_1$–$C_4$-alkoxy-$C_1$–$C_4$-alkyl, $C_1$–$C_4$-alkylthio-$C_1$–$C_4$-alkyl, $C_1$–$C_4$-alkoxy, $C_1$–$C_4$-alkylthio or $C_3$–$C_6$-cycloalkyl which is optionally mono- to trisubstituted by identical or different $C_1$–$C_4$-alkyl or halogen substituents, $R^2$ preferably represents hydrogen, $C_1$–$C_4$-alkyl, $C_1$–$C_4$-halogenoalkyl having 1 to 5 identical or different halogen atoms, such as fluorine and chlorine atoms, $C_1$–$C_4$-alkoxy-$C_1$–$C_4$-alkyl, $C_1$–$C_4$-alkyl-carbonyl, $C_1$–$C_4$-alkylsulphonyl, phenylcarbonyl, phenylsulphonyl or benzyl, each of which is optionally mono- to trisubstituted on the phenyl ring by identical or different substituents from the group consisting of halogen, nitro, cyano, $C_1$–$C_4$-alkyl, $C_1$–$C_2$-halogenoalkyl having 1 to 5 identical or different halogen atoms, such as fluorine and chlorine atoms, $C_1$–$C_4$-alkoxy, $C_1$–$C_4$-alkylthio, $C_1$–$C_2$-halogenoalkoxy having 1 to 5 identical or different halogen atoms, such as fluorine and chlorine atoms, or $C_1$–$C_2$-halogenoalkylthio having 1 to 5 identical or different halogen atoms, such as fluorine and chlorine atoms, or represents $C_3$–$C_6$-cycloalkyl which is optionally mono- to trisubstituted by identical or different $C_1$–$C_4$-alkyl or halogen substituents, $R^3$ preferably represents phenyl which is optionally mono- to trisubstituted by identical or different substituents from the group consisting of halogen, nitro, cyano, $C_1$–$C_{12}$-alkyl, $C_1$–$C_{12}$-halogenoalkyl having 1 to 5 identical or different halogen atoms, such as fluorine and chlorine atoms, $C_1$–$C_{12}$-alkoxy, $C_1$–$C_{12}$-halogenoalkoxy having 1 to 5 identical or different halogen atoms, such as fluorine and chlorine atoms, $C_1$–$C_{12}$-alkylthio, $C_1$–$C_{12}$-halogenoalkylthio having 1 to 5 identical or different halogen atoms, such as fluorine and chlorine atoms, $C_2$–$C_{12}$-alkenyl, $C_2$–$C_{12}$-halogenoalkenyl having 1 to 5 identical or different halogen atoms, such as fluorine and chlorine atoms, $C_3$–$C_8$-cycloalkyl which is optionally mono- to trisubstituted by identical or different $C_1$–$C_4$-alkyl or halogen substituents, and phenyl, phenoxy, phenylthio or benzyl, each of which is optionally mono- to trisubstituted by identical or different substituents from the group consisting of halogen, nitro, cyano, $C_1$–$C_4$-alkyl, $C_1$–$C_4$-halogenoalkyl having 1 to 5 identical or different halogen atoms, such as fluorine and chlorine atoms, $C_1$–$C_4$-alkoxy, $C_1$–$C_4$-halogenoalkoxy having 1 to 5 identical or different halogen atoms, such as fluorine and chlorine atoms, $C_1$–$C_4$-alkylthio, $C_1$–$C_4$-halogenoalkylthio having 1 to 5 identical or different halogen atoms, such as fluorine and chlorine atoms, $C_1$–$C_4$-alkylthio-$C_1$–$C_4$-alkyl, $C_1$–$C_4$-alkylsulphonyl, $C_1$–$C_4$-halogenoalkylsulphonyl having 1 to 5 identical or different halogen atoms, such as fluorine and chlorine atoms, and $C_1$–$C_4$-alkoxycarbonyl, or represents $C_3$–$C_8$-cycloalkyl or $C_5$–$C_8$-cycloalkenyl, each of which is optionally mono- to trisubstituted by identical or different substituents from the group consisting of $C_1$–$C_4$-alkyl, $C_1$–$C_4$-halogenoalkyl having 1 to 5 identical or different halogen atoms, such as fluorine and chlorine atoms, $C_1$–$C_4$-alkoxy, $C_1$–$C_4$-halogenoalkoxy having 1 to 5 identical or different halogen atoms, such as fluorine and chlorine atoms, $C_3$–$C_8$-cycloalkyl, and phenyl which is optionally mono- to trisubstituted by identical or different substituents from the group consisting of halogen, cyano, nitro, $C_1$–$C_4$-alkyl, $C_1$–$C_4$-halogenoalkyl having 1 to 5 identical or different halogen atoms, such as fluorine and chlorine atoms, $C_1$–$C_4$-alkoxy and $C_1$–$C_4$-halogenoalkoxy having 1 to 5 identical or different halogen atoms, such as fluorine and chlorine atoms, and Y preferably represents $C_1$–$C_6$-alkylene, $C_1$–$C_6$-hydroxyalkylene, $C_1$–$C_4$-alkoxy-$C_1$–$C_6$-alkylene, $C_1$–$C_4$-alkylcarbonyloxy-$C_1$–$C_6$-alkylene, cyano-$C_1$–$C_6$-alkylene, $C_1$–$C_4$-halogenoalkylene having 1 to 5 identical or different halogen atoms, such as fluorine and chlorine atoms; or $C_3$–$C_6$-cycloalkyl-$C_1$–$C_4$-alkylene, $C_2$–$C_4$-alkenylene or $C_1$–$C_4$-alkyleneoxy, each of which is optionally mono- to trisubstituted by identical or different substituents from the group consisting of fluorine, chlorine and methyl.

$R^1$ particularly preferably represents methyl, ethyl, n- or i-propyl, n-, i-, s- or t-butyl; $CH_2F$, $CHF_2$, $CF_3$, $CH_2Cl$, $CH_2Br$, $CHClCH_3$; methoxy, ethoxy, methoxymethyl, ethoxymethyl; methylthiomethyl or cyclopropyl, $R^2$ particularly preferably represents hydrogen, methyl, ethyl, n- or i-propyl; methoxymethyl, ethoxymethyl, n-propoxymethyl, n-butoxymethyl; methylcarbonyl, methylsulphonyl; phenylcarbonyl or benzyl, each of which is optionally mono- or disubstituted by identical or different substituents from the group consisting of fluorine, chlorine, methyl or trifluoromethyl; or cyclopropyl, $R^3$ particularly preferably represents phenyl which is optionally mono- to trisubstituted by identical or different substituents from the group consisting of halogen, nitro, cyano, $C_1$–$C_{12}$-alkyl, $C_1$–$C_{12}$-halogenoalkyl having 1 to 5 identical or different halogen atoms, such as fluorine and chlorine atoms, $C_1$–$C_4$-alkoxy, $C_1$–$C_4$-halogenoalkoxy having 1 to 5 identical or different halogen atoms, such as fluorine and chlorine atoms, $C_1$–$C_4$-alkylthio, $C_1$–$C_4$-halogenoalkylthio having 1 to 5 identical or different halogen atoms, such as fluorine and chlorine atoms, $C_2$–$C_4$-alkenyl, $C_2$–$C_4$-halogenoalkenyl having 1 to 5 identical or different halogen atoms, such as fluorine and chlorine atoms, and phenoxy or phenylthio, each of which is optionally mono- to trisubstituted by identical or different substituents from the group consisting of halogen, nitro, cyano, $C_1$–$C_4$-alkyl, $C_1$–$C_4$-halogenoalkyl having 1 to 5 identical or different halogen atoms, such as fluorine and chlorine atoms, $C_1$–$C_4$-alkoxy, $C_1$–$C_4$-halogenoalkoxy having 1 to 5 identical or different halogen atoms, such as fluorine and chlorine atoms, $C_1$–$C_4$-alkylthio, $C_1$–$C_4$-halogenoalkylthio having 1 to 5 identical or different halogen atoms, such as fluorine and chlorine atoms, $C_1$–$C_4$-alkylthio-$C_1$–$C_4$-alkyl, $C_1$–$C_4$-alkylsulphonyl, $C_1$–$C_4$-halogenoalkylsulphonyl having 1 to 5 identical or different halogen atoms, such as fluorine and chlorine atoms, and $C_1$–$C_4$-alkoxy-carbonyl.

Y particularly preferably represents one of the groups —$CH_2$—, —$CH(CH_3)$—, —$CH(C_2H_5)$—, —$CH(n$-$C_3H_7)$—, —$CH(i$-$C_3H_7)$—, —$CH_2CH_2$—, —$CH(OH)$—, —$CH(OCH_3)$—, —$CH(O$—$CO$—$CH_3)$—, —$CH(CN)$—, —$CHF$—, —$CHCl$—, —CH— 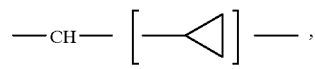 —, —CH=CH— or —$CH_2O$—.

$R^1$ very particularly preferably represents methyl, ethyl, n- or i-propyl, n-, i-, s- or t-butyl; $CH_2F$, $CHF_2$, $CF_3$, $CH_2Cl$, $CH_2Br$, methoxy, ethoxy or cyclopropyl, $R^2$ very particularly preferably represents hydrogen, methyl, ethyl, methoxymethyl, ethoxymethyl, methylcarbonyl, phenylcarbonyl or methylsulphonyl, $R^3$ very particularly preferably represents phenyl which is optionally mono- to trisubstituted by identical or different substituents from the group consisting of fluorine, chlorine, bromine, nitro, cyano, methyl, ethyl, n- or i-propyl, n-, i-, s- or t-butyl; methoxy, ethoxy, n- or i-propoxy, n-, i-, s- or t-butoxy; methylthio, $CF_3$, $OCF_3$, $OCHF_2$, $SCF_3$, $SCCl_2F$, $CH_2Br$, $CH_2Cl$, and phenoxy which is optionally mono- to trisubstituted by identical or different substituents from the group consisting of fluorine, chlorine, bromine, nitro, cyano, methyl, ethyl, n- or i-propyl, n-, i-, s- or t-butyl, methoxy, ethoxy, n- or i-propoxy, n-, i-, s- or t-butoxy, methylthio, methylthiomethyl, $CF_3$, $OCF_3$, $OCHF_2$, $SCF_3$, $SCCl_2F$, $CH_2Br$, $CH_2Cl$, methoxycarbonyl, methylsulphonyl and trifluoromethylsulphonyl, and Y very particularly preferably represents —$CH_2$—, —$CH(CH_3)$—, —$CH_2CH_2$— or —CH=CH—.

Preferred compounds according to the invention are substances of the formulae (IA) and (IB):

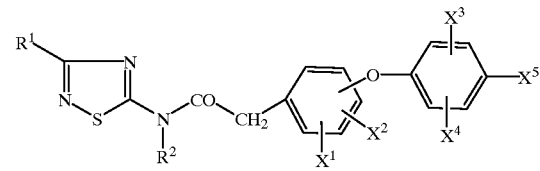

(IA)

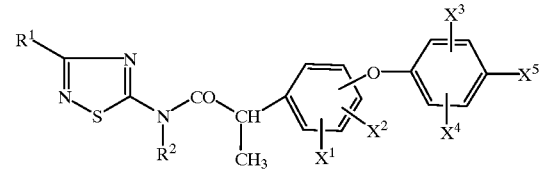

(IB)

in which $R^1$ and $R^2$ each have the abovementioned general, preferred, particularly preferred and very particularly preferred meanings and $X^1$, $X^2$, $X^3$, $X^4$ and $X^5$ each represent the substituents listed above under $R^3$ as general, preferred, particularly preferred and very particularly preferred for the phenyl or phenoxy radical and $X^1$, $X^2$, $X^3$ and $X^4$ each may also represent hydrogen.

A further preferred group of compounds are those of the formulae (IA) or (IB) in which the phenoxy radical is para to the $NR^2$—CO—$CH_2$— or $NR^2$—CO—$CH(CH_3)$ group. Of these compounds, those particularly preferred are compounds in which the substituents $X^1$, $X^2$, $X^3$ and $X^4$ each represent hydrogen.

The abovementioned general and preferred definitions of radicals or illustrations apply both to the end products and to the corresponding precursors and intermediates. These definitions can be combined with each other as desired, that is to say combinations between the respective preferred ranges are also possible.

For the purpose of the invention, preference is given to compounds of the formula (I) in which there exists a combination of the meanings mentioned above as preferred (preferable).

For the purpose of the invention, particular preference is given to compounds of the formula (I) in which there exists a combination of the meanings mentioned above as particularly preferred.

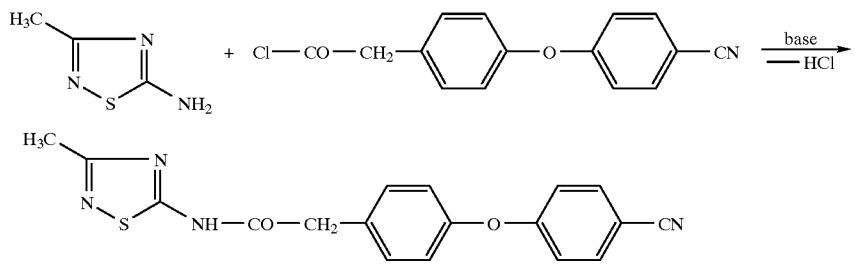

For the purpose of the invention, very particular preference is given to the compounds of the formula (I) in which there exists a combination of the meanings mentioned above as very particularly preferred.

In the definitions of radicals mentioned hereinabove and hereinbelow, hydrocarbon radicals such as alkyl or alkenyl can in each case be—even in combination with hetero atoms such as alkoxy or alkylthio—straight-chain or branched as far as this is possible.

Besides the Preparation Examples, specific examples of the compounds of the formula (IC) include:

TABLE A (IC)

| $R^1$ | $R^2$ | Y | X |
|---|---|---|---|
| $C_2H_5$ | H | $CH_2$ | 4-CN |
| $C_2H_5$ | H | $CH_2$ | 4-$NO_2$ |
| $C_2H_5$ | H | $CH_2$ | 4-Cl |
| $C_2H_5$ | H | $CH_2$ | 4-$OCF_3$ |
| $C_2H_5$ | H | $CH_2$ | 4-$CF_3$ |
| $C_2H_5$ | H | $CH_2$ | 4-$SCF_3$ |
| $C_2H_5$ | H | $CH_2$ | 4-$SCH_3$ |
| $C_2H_5$ | H | $CH_2$ | 4-$SO_2CH_3$ |
| $C_2H_5$ | H | $CH_2$ | 4-$SO_2CF_3$ |
| $C_2H_5$ | H | $CH_2$ | 4-$CO_2CH_3$ |
| $C_2H_5$ | H | $CHCH_3$ | 4-CN |
| $C_2H_5$ | H | $CHCH_3$ | 4-$NO_2$ |
| $C_2H_5$ | H | $CHCH_3$ | 4-Cl |
| $C_2H_5$ | H | $CHCH_3$ | 4-$OCF_3$ |
| $C_2H_5$ | H | $CHCH_3$ | 4-$CF_3$ |
| $C_2H_5$ | H | $CHCH_3$ | 4-$SCF_3$ |
| $C_2H_5$ | H | $CHCH_3$ | 4-$SCH_3$ |
| $C_2H_5$ | H | $CHCH_3$ | 4-$SO_2CH_3$ |
| $C_2H_5$ | H | $CHCH_3$ | 4-$SO_2CF_3$ |
| $C_2H_5$ | H | $CHCH_3$ | 4-$CO_2CH_3$ |
| $C_2H_5$ | H | $CH_2CH_2$ | 4-CN |
| $C_2H_5$ | H | CHCH | 4-CN |
| $C_2H_5$ | H | $CH_2O$ | 4-CN |
| $C_2H_5$ | $CH_3$ | $CH_2$ | 4-CN |
| $C_2H_5$ | $CH_3$ | $CH_2$ | 4-$NO_2$ |
| $C_2H_5$ | $CH_3$ | $CH_2$ | 4-$OCF_3$ |
| $C_2H_5$ | $CH_3$ | $CH_2$ | 4-Cl |
| $C_2H_5$ | $COCH_3$ | $CH_2$ | 4-CN |

If, for example, 5-amino-3-methyl-1,2,4-thiadiazole and [4-(4-cyano)phenoxy]-phenyl-acetyl chloride are used as starting materials for the preparation of compounds of the formula (I), the course of the reaction of the process according to the invention can be represented by the following scheme:

The 5-amino-1,2,4-thiadiazoles of the formula (II) to be used as starting materials in the process according to the invention are known (cf. for example EP-A-0 455 356; Gazz. Chim. Ital. 1977, 107, p. 1ff or Chem. Ber. 195, 87, p. 57ff) and/or can be prepared by known methods (cf. for example the abovementioned literature references).

The acid halides of the formula (III) further to be used as starting materials in the process according to the invention are generally known compounds of organic chemistry. In the formula (III), Hal represents preferably chlorine or bromine.

The process according to the invention for preparing the compounds of the formula (I) is carried out in the presence of a diluent. Suitable diluents are all customary diluents. Preferred diluents are optionally halogenated aliphatic or aromatic hydrocarbons, ethers or nitriles, such as, for example, cyclohexane, toluene, chlorobenzene, chloroform, dichloromethane, dichloroethane, dioxane, tetrahydrofuran, diethyl ether or acetonitrile.

The process according to the invention for preparing compounds of the formula (I) is carried out in the presence of a base.

Suitable bases are all customary proton acceptors. Preferred bases are alkali metal hydroxides or alkaline earth metal hydroxides, alkali metal carbonates or alkaline earth metal carbonates, alkali metal hydrogen carbonates or alkaline earth metal hydrogen carbonates or nitrogen bases. Examples include sodium hydroxide, calcium hydroxide, potassium carbonate, sodium hydrogen carbonate, triethylamine, dibenzylamine, diisopropylamine, pyridine, quinoline, diazabicyclooctane (DABCO), diazabicyclononene (DBN) and diazabicycloundecene (DBU).

The reaction temperatures of the process according to the invention may be varied over a relatively wide range. In general, the process is carried out at temperatures between −40° C. and +200° C., preferably between 0° C. and 100° C.

When carrying out the process according to the invention, in general 1 to 2 mol, preferably 1 to 1.5 mol, of acid halide of the formula (III) are employed per mole of 5-amino-1,2,4-thiadiazole of the formula (II).

In some cases it is advantageous to employ the 5-amino-1,2,4-thiadiazoles of the formula (II) in the form of their hydrohalides, such as in particular as hydrochlorides.

Work-up and isolation of the end products is carried out in a customary manner.

The active compounds are suitable for combating animal pests, in particular insects, arachnids and nematodes, encountered in agriculture, in forestry, in the protection of stored products and of materials, and in the hygiene field, and have good plant tolerance and favourable toxicity to warm-blooded animals. They may preferably be employed as crop protection agents. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and *Scutigera spec.*

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus,* Gryllotalpa spp., *Locusta migratoria migratoioides, Melanoplus differentialis* and *Schistocerca gregaria.*

From the order of the Dermaptera, for example, *Forficula auricularia.*

From the order of the Isoptera, for example, Reticulitermes spp.

From the order of the Anoplura, for example, *Pediculus humanus corporis,* Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci.*

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix,* Pemphigus spp., *Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Spodoptera litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.*

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.*

From the order of the Siphonaptera, for example, *Xenopsylla cheopis* and Ceratophyllus spp.

From the order of the Arachnida, for example, *Scorpio maurus, Latrodectus mactans.*

From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp., Tetranychus spp.

The phytoparasitic nematodes include, for example, Pratylenchus spp., *Radopholus similis, Ditylenchus dipsaci, Tylenchulus semipenetrans,* Heterodera spp., Globodera spp., Meloidogyne spp., Aphelenchoides spp., Longidorus spp., Xiphinema spp., Trichodorus spp.

The compounds of the formula (I) according to the invention have, in particular, a high insecticidal and acaricidal activity.

They are employed particularly successfully for controlling plant-damaging insects, for example against mustard beetle larvae (*Phaedon cochlaeriae*), caterpillars of the diamondback moth (*Plutella maculipennis*), green rice leaf hoppers (*Nephotettix cinctriceps*), aphids (*Mycus persicae*) and caterpillars of the owlet moth (*Spodoptera frugiperda*) or for controlling plant-damaging mites, for example against spider mites (*Tetranychus urticae*).

The compounds according to the invention have a potent microbicidal activity and can be employed for controlling undesirable microorganisms such as fungi and bacteria, in crop protection and in the protection of materials.

Fungicides are employed in crop protection for controlling Plasmodiophoromycetes, Oomycetes, Chytridiomycetes, Zygomycetes, Ascomycetes, Basidiomycetes and Deuteromycetes.

Bactericides are employed in crop protection for controlling Pseudomonadaceae, Rhizobiaceae, Enterobacteriaceae, Corynebacteriaceae and Streptomycetaceae.

Some pathogens causing fungal and bacterial diseases which come under the generic names listed above may be mentioned as examples, but not by way of limitation:

Xanthomonas species, such as, for example, *Xanthomonas campestris* pv. oryzae;

Pseudomonas species, such as, for example, *Pseudomonas syringae* pv. lachrymans;

Erwinia species, such as, for example, *Erwinia amylovora;*

Pythium species, such as, for example, *Pythium ultimum;*

Phytophthora species, such as, for example, *Phytophthora infestans;*

Pseudoperonospora species, such as, for example, *Pseudoperonospora humuli* or *Pseudoperonospora cubensis;*

Plasmopara species, such as, for example, *Plasmopara viticola;*
Bremia species, such as, for example, *Bremia lactucae,*
Peronospora species, such as, for example, *Peronospora pisi* or *P. brassicae;*
Erysiphe species, such as, for example, *Erysiphe graminis;*
Sphaerotheca species, such as, for example, *Sphaerotheca fuliginea;*
Podosphaera species, such as, for example, *Podosphaera leucotricha;*
Venturia species, such as, for example, *Venturia inaequalis;*
Pyrenophora species, such as, for example, *Pyrenophora teres* or *P. graminea* (conidia form: Drechslera, syn: Helminthosporium);
Cochliobolus species, such as, for example, *Cochliobolus sativus* (conidia form: Drechslera, syn: Helminthosporium);
Uromyces species, such as, for example, *Uromyces appendiculatus;*
Puccinia species, such as, for example, *Puccinia recondita;*
Sclerotinia species, such as, for example, *Sclerotinia sclerotiorum*
Tilletia species, such as, for example, *Tilletia caries;*
Ustilago species, such as, for example, *Ustilago nuda* or *Ustilago avenae;*
Pellicularia species, such as, for example, *Pellicularia sasakii;*
Pyricularia species, such as, for example, *Pyricularia oryzae;*
Fusarium species, such as, for example, *Fusarium culmorum;*
Botrytis species, such as, for example, *Botrytis cinerea;*
Septoria species, such as, for example, *Septoria nodorum;*
Leptosphaeria species, such as, for example, *Leptosphaeria nodorum;*
Cercospora species, such as, for example, *Cercospora canescens;*
Alternaria species, such as, for example, *Alternaria brassicae* and
Pseudocercosporella species, such as, for example, *Pseudocercosporella herpotrichoides.*

The fact that the active compounds are well tolerated by plants at the concentrations required for controlling plant diseases permits the treatment of aerial parts of plants, of propagation stock and seeds, and of the soil.

The active compounds according to the invention can be employed successfully for controlling diseases in fruit and vegetable growing and viticulture, such as, for example, against Plasmopara species. They are also very successfully used for controlling cereal diseases, such as, for example, against Cochliobolus-, Leptosphaeria- and Erysiphe species, or for controlling rice diseases, such as, for example, against the pathogen causing rice blast disease (*Pyricularia oryzae*). Furthermore, the compounds according to the invention may also be employed to increase the yield of crops.

In the protection of materials, the substances according to the invention can be employed for protecting industrial materials against infection with, and destruction by, undesired microorganisms.

Industrial materials in the present context are understood as meaning non-live materials which have been prepared for use in industry. For example, industrial materials which are intended to be protected by active compounds according to the invention from microbial change or destruction can be glues, sizes, paper and board, textiles, leather, wood, paints and plastic articles, cooling lubricants and other materials which can be infected with, or destroyed by, microorganisms. Parts of production plants, for example cooling-water circuits, which may be impaired by the multiplication of microorganisms may also be mentioned within the scope of the materials to be protected. Industrial materials which may be mentioned within the scope of the present invention are preferably glues, sizes, papers and boards, leather, wood, paints, cooling lubricants and heat-transfer liquids.

Microorganisms, capable of bringing about degradation of, or change in, the industrial materials, which may be mentioned are, for example, bacteria, fungi, yeasts, algae and slime organisms. The active compounds or agents according to the invention preferably act against fungi, in particular moulds, and against slime organisms and algae.

Microorganisms of the following genera may be mentioned as examples:
Alternaria, such as *Alternaria tenuis,*
Aspergillus, such as *Aspergillus niger,*
Chaetomium, such as *Chaetomium globosum,*
Coniophora, such as *Coniophora puetana,*
Lentinus, such as *Lentinus tigrinus,*
Penicillium, such as *Penicillium glaucum,*
Polyporus, such as *Polyporus versicolor,*
Aureobasidium, such as *Aureobasidium pullulans,*
Sclerophoma, such as *Sclerophoma pityophila,*
Trichoderma, such as *Trichoderma viride,*
Escherichia, such as *Escherichia coli,*
Pseudomonas, such as *Pseudomonas aeruginosa* and
Staphylococcus, such as *Staphylococcus aureus.*

Depending on their particular physical and/or chemical properties, the active compounds can be converted to the customary formulations, such as solutions, emulsions, suspensions, powders, foams, pastes, granules, aerosols and microencapsulations in polymeric substances and in coating compositions for seeds, and ULV cooled and warm fogging formulations.

These formulations are produced in a known manner, for example by mixing the active compounds with extenders, that is, liquid solvents, liquefied gases under pressure, and/or solid carriers, optionally with the use of surfactants, that is emulsifiers and/or dispersants, and/or foam formers. In the case of the use of water as an extender, organic solvents can, for example, also be used as auxiliary solvents. The following are mainly suitable as liquid solvents: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water. Liquefied gaseous extenders or carriers are to be understood as meaning liquids which are gaseous at ambient temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as highly disperse silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example non ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other additives can be mineral and vegetable oils.

It is possible to use colourants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 per cent by weight of active compound, preferably between 0.5 and 90%.

The active compounds according to the invention can be used as such or in their formulations also mixed with known fungicides, bactericides, acaricides, nematicides or insecticides in order thus, for example, to widen the spectrum of action or to prevent development of resistance. In many cases, synergistic effects are achieved, i.e. the activity of the mixture exceeds the activity of the individual components.

Examples of co-components in mixtures are the following compounds:
Fungicides:
aldimorph, ampropylfos, ampropylfos potassium, andoprim, anilazine, azaconazole, azoxystrobin,
benalaxyl, benodanil, benomyl, benzamacril, benzamacril-isobutyl, bialaphos, binapacryl, biphenyl, beternatol, blasticidin-S, bromuconazole, bupirimate, buthiobate,
calcium polysulphide, capsimycin, captafol, captan, carbendazim, carboxin, carvon, quinomethionate, chlobenthiazone, chlorfenazole, chloroneb, chloropicrin, chlorothalonil, chlozolinate, chlozylacon, cufraneb, cymoxanil, cyproconazole, cyprodinil, cyprofuram,
debacarb, dichlorophen, diclobutrazol, diclofluanid, diclomezine, dicloran, diethofencarb, difenoconazole, dimethirimol, dimethomorph, diniconazole, diniconazol-M, dinocap, diphenylamine, dipyrithione, ditalimfos, dithianon, dodemorph, dodine, drazoxolon,
edifenphos, epoxiconazole, etaconazole, ethirimol, etridiazole,
famoxadon, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulfamide, flutolanil, flutriafol, folpet, fosetyl-aluminium, fosetyl-sodium, fthalide, fuberidazole, furalaxyl, furametpyr, furcarbanil, furconazole, furconazolecis, furmecyclox,
guazatine,
hexachlorobenzene, hexaconazole, hymexazol,
imazalil, imibenconazole, iminoctadine, iminoctadine albesilate, iminoctadine triacetate, iodocarb, ipconazole, iprobenfos (IBP), iprodione, irumamycin, isoprothiolane, isovaledione,
kasugamycin, kresoxim-methyl, copper preparations, such as: copper hydroxide, copper naphthenate, copper oxychloride, copper sulphate, copper oxide, oxine-copper and Bordeaux mixture,
mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin, nickel bis (dimethyldithiocarbamate), nitrothal-isopropyl, nuarimol, ofurace, oxadixyl, oxamocarb, oxolinic acid, oxycarboxin, oxyfenthiin, paclobutrazol, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, pyrazophos, pyrifenox, pyrimethanil, pyroquilon, pyroxyfur,
quinconazole, quintozene (PCNB),
sulphur and sulphur preparations,
tebuconazole, tecloftalam, tecnazene, tetcyclasis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, triflumizole, triforine, triticonazole, uniconazole,
validamycin A, vinclozolin, viniconazole,
zaliramide, zineb, ziram and also
Dagger G,
OK-8705,
OK-8801,
α-(1,1-dimethylethyl)-β-(2-phenoxyethyl)-1H-1,2,4-triazole-1-ethanol,
α-(2,4-dichlorophenyl)-β-fluoro-β-propyl-1H-1,2,4-triazole-1-ethanol,
α-(2,4-dichlorophenyl)-β-methoxy-α-methyl-1H-1,2,4-triazole-1-ethanol,
α-(5-methyl-1,3-dioxan-5-yl)-β-[[4-trifluoromethyl)-phenyl]-methylene]-1H-1,2,4-triazole-1-ethanol,
(5RS,6RS)-6-hydroxy-2,2,7,7-tetramethyl-5-(1H-1,2,4-triazol-1-yl)-3-octanone,
(E)-α-(methoxyimino)-N-methyl-2-phenoxy-phenylacetamide, isopropyl {2-methyl-1-[[[1-(4-methylphenyl)-ethyl]-amino]-carbonyl]-propyl}-carbamate,
1-(2,4-dichlorophenyl)-2-(1H-1,2,4-triazol-1-yl)ethanone-O-(phenylmethyl)-oxime,
1-(2-methyl-1-naphthalenyl)-1H-pyrrol-2,5-dione,
1-(3,5-dichlorophenyl)-3-(2-propenyl)-2,5-pyrrolidindione,
1-[(diiodomethyl)-sulphonyl]-4-methyl-benzene
1-[[2-(2,4-dichlorophenyl)-1,3-dioxolan-2-yl]-methyl]-1H-imidazole,
1-[[2-(4-chlorophenyl)-3-phenyloxiranyl]-methyl]-1H-1,2,4-triazole,
1-[1-[2-[(2,4-dichlorophenyl)-methoxy]-phenyl]-etheneyl]-1H-imidazole,
1-methyl-5-nonyl-2-(phenylmethyl)-3-pyrrolidinole,
2',6'-dibromo-2-methyl-4'-trifluoromethoxy-4'-trifluoro-methyl-1,3-thiazol-5-carboxanilide,
2,2-dichloro-N-[1-(4-chlorophenyl)-ethyl]-1-ethyl-3-methyl-cyclopropanecarboxamide,
2,6-dichloro-5-(methylthio)-4-pyrimidinyl-thiocyanate,
2,6-dichloro-N-(4-trifluoromethylbenzyl)-benzamide,
2,6-dichloro-N-[[4-trifluoromethyl)-phenyl]-methyl]-benzamide,
2-(2,3,3-triiodo-2-propenyl)-2H-tetrazole,
2-[(1-methylethyl)sulphonyl]-5-trichloromethyl)-1,3,4-thiadiazole,
2-[[6-deoxy-4-O-(4-O-methyl-β-D-glycopyranosyl)-α-D-glucopyranosyl]-amino]-4-methoxy-1H-pyrrolo[2,3-d]pyrimidine-5-carbonitrile,
2-aminobutane,
2-bromo-2-(bromomethyl)-pentandinitrile, 2-chloro-N-(2,3-dihydro-1,1,3-trimethyl-1H-inden-4-yl)-3-pyridinecarboxamide,
2-chloro-N-(2,6-dimethylphenyl)-N-(isothiocyanatomethyl)-acetamide,
2-phenylphenol (OPP),
3,4-dichloro-1-[4-(difluoromethoxy)-phenyl]-1H-pyrrol-2,5-dione,
3,5-dichloro-N-[cyano-[(1-methyl-2-propynyl)-oxy]-methyl]-benzamide,
3-(1,1-dimethylpropyl-1-oxo-1H-indene-2-carbonitrile,
3-[2-(4-chlorophenyl)-5-ethoxy-3-isoxazolidinyl]-pyridine,
4-chloro-2-cyano-N,N-dimethyl-5-(4-methylphenyl)-1H-imidazole-1-sulfonamide,
4-methyl-tetrazolo[1,5-a]quinazolin-5(4H)-one
8-(1,1-dimethylethyl)-N-ethyl-N-propyl-1,4-dioxaspiro[4.5]decane-2-methanamine,
8-hydroxyquinoline sulfate
9H-xanthene-2-[(phenylamino)-carbonyl]-9-carboxylic hydrazide,
bis-(1-methylethyl)-3-methyl-4-[(3-methylbenzoyl)oxy]-2,5-thiophenedicarboxylate,
cis-1-(4-chlorophenyl)-2-(1H-1,2,4-triazol-1-yl)-cycloheptanol,
cis-4-[3-[4-(1,1-dimethylpropyl)-phenyl-2-methylpropyl]-2,6-dimethyl-morpholinehydrochloride,
ethyl[(4-chlorophenyl)-azo]-cyanoacetate
potassium hydrogencarbonate
methanetetrathiol sodium salt
methyl 1-(2,3-dihydro-2,2-dimethyl-1H-inden-1-yl)-1H-imidazole-5-carboxyl-ate,
methyl N-(2,6-dimethylphenyl)-N-(5-isoxazolylcarbonyl)-DL-alaninate,
methyl N-(chloroacetyl)-N-(2,6-dimethylphenyl)-DL-alaninate,
N-(2,3-dichloro-4-hydroxyphenyl)-1-methyl-cyclohexanecarboxamide,
N-(2,6-dimethylphenyl)-2-methoxy-N-(tetrahydro-2-oxo-3-furanyl)-acetamide,
N-(2,6-dimethylphenyl)-2-methoxy-N-(tetrahydro-2-oxo-3-thienyl)-acetamide,
N-(2-chloro-4-nitrophenyl)-4-methyl-3-nitrobenzenesulfonamide,
N-(4-cyclohexylphenyl)-1,4,5,6-tetrahydro-2-pyrimidinamine,
N-(4-hexylphenyl)-1,4,5,6-tetrahydro-2-pyrimidinamine,
N-(5-chloro-2-methylphenyl)-2-methoxy-N-(2-oxo-3-oxazolidinyl)-acetamide,
N-(6-methoxy)-3-pyridinyl)-cyclopropanecarboxamide,
N-[2,2,2-trichloro-1-[(chloroacetyl)-amino]-ethyl]-benzamide,
N-[3-chloro-4,5-bis(2-propinyloxy)-phenyl]-N'-methoxy-methanimidamide,
N-formyl-N-hydroxy-DL-alanine-monosodium salt
O,O-diethyl [2-(dipropylamino)-2-oxoethyl]-ethylphosphoramidothioate,
O-methyl S-phenyl phenylpropylphosphoramidothioate,
S-methyl 1,2,3-benzothiadiazole-7-carbothioate,
spiro[2H]-1-benzopyrane-2,1'(3'H)-isobenzofuran]-3'-one,
Bactericides:
bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations
Insecticides/Acaricides/Nematicides:
abamectin, acephate, acrinathrin, alanycarb, aldicarb, alphamethrin, amitraz, avermectin, AZ 60541, azadirachtin, azinphos A, azinphos M, azocyclotin,
Bacillus thuringiensis, 4-bromo-2-(4-chlorophenyl)-1-(ethoxymethyl)-5-(tri-fluoromethyl)-1H-pyrrole-3-carbonitrile, bendiocarb, benfuracarb, bensultap, betacyfluthrim, bifenthrin, BPMC, brofenprox, bromophos A, bufencarb, buprofezin, butocarboxim, butylpyridaben,
cadusafos, carbaryl, carbofuran, carbophenothion, carbosulfan, cartap, chloethocarb, chlorethoxyfos, chlorfenapyr, chlorfenvinphos, chlorfluazuron, chlormephos, N-[(6-chloro-3-pyridinyl)-methyl]-N'-cyano-N-methyl-ethanimidamide, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine,
deltamethrin, demeton M, demeton S, demeton S-methyl, diafenthiuron, diazinon, dichlofenthion, dichlorvos, dicliphos, dicrotophos, diethion, diflubenzuron, dimethoate, dimethylvinphos, dioxathion, disulfoton,
edifenphos, emamectin, esfenvalerate, ethiofencarb, ethion, ethofenprox, ethoprophos, etrimphos,
fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, fluazuron, flucycloxuron, flucythrinate, flufenoxuron, flufenprox, fluvalinate, fonophos, formothion, fosthiazate, fubfenprox, furathiocarb,
HCH, heptenophos, hexaflumuron, hexythiazox,
imidacloprid, iprobenfos, isazophos, isofenphos, isoprocarb, isoxathion, ivermectin,
lambda-cyhalothrin, lufenuron,
malathion, mecarbam, mevinphos, mesulfenphos, metaldehyde, methacrifos, methamidophos, methidathion, methiocarb, methomyl, metolcarb, milbemectin, monocrotophos, moxidectin,
naled, NC 184, nitenpyram,
omethoate, oxamyl, oxydemethon M, oxydeprofos,
parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozin, pyrachlophos, pyridaphenthion, pyresmethrin, pyrethrum, pyridaben, pyrimidifen, pyriproxifen,
quinalphos,
salithion, sebufos, silafluofen, sulfotep, sulprofos,
tebufenozide, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb,
vamidothion, XMC, xylylcarb, zetamethrin.

It is also possible to admix other known active compounds, such as herbicides, or fertilizers and growth-promoting substances.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compounds can be used as such or in the form of their commercial formulations or the use forms prepared therefrom, such as ready-to-use solutions, suspensions, wettable powders, pastes, soluble powders, dusts and granules. They are used in the customary manner, for example by wetting, spraying, atomizing, spreading, foaming, brushing on and the like. It is further possible to apply the active compounds by the ultra-low volume method or to inject the active compound formulation, or the active compound itself, into the soil. The seed of the plants can also be treated.

In the treatment of parts of plants, the active compound concentrations in the use forms can be varied within a substantial range. They are, in general, between 1 and 0.0001% by weight, preferably between 0.5 and 0.001% by weight.

In the treatment of seed, amounts of active compound of from 0.001 to 50 g, preferably 0.01 to 10 g, are generally required per kilogram of seed.

In the treatment of the soil, active compound concentrations of from 0.00001 to 0.1% by weight, preferably from 0.0001 to 0.02% by weight, are required at the site of action.

The compositions used for the protection of industrial materials generally comprise an amount of 1 to 95%, preferably 10 to 75%, of the active compounds.

The use concentrations of the active compounds according to the invention depend on the species and the occurrence of the microorganisms to be controlled and on the composition of the material to be protected. The optimal rate of application can be determined by test series. In general, the use concentrations are in the range of from 0.001 to 5% by weight, preferably 0.05 to 1.0% by weight, based on the material to be protected.

The compounds are employed in a customary manner appropriate for the use forms.

When used against hygiene pests and pests in stored products, the active compound is distinguished by an excellent residual action on wood and clay as well as a good stability to alkali on limed substrates.

The active compounds according to the invention are not only active against plant, hygiene and stored-product pests, but also, in the veterinary medicine sector, against animal parasites (ectoparasites), such as ixodid ticks, argasid ticks, scab mites, trombiculid mites, flies (stinging and sucking), parasitic fly larvae, lice, hair lice, bird lice and fleas. These parasites include:

From the order of the Anoplurida, for example, Haematopinus spp., Linognathus spp., Pediculus spp., Phtirus spp., Solenopotes spp.

From the order of the Mallophagida and the sub-orders Amblycerina and Ischnocerina, for example, Trimenopon spp., Menopon spp., Trinoton spp., Bovicola spp., Werneckiella spp., Lepikentron spp., Damalina spp., Trichodectes spp., Felicola spp.

From the order of the Diptera and the sub-orders Nematocerina and Brachycerina, for example, Aedes spp., Anopheles spp., Culex spp., Simulium spp., Eusimulium spp., Phlebotomus spp., Lutzomyia spp., Culicoides spp., Chrysops spp., Hybomitra spp., Atylotus spp., Tabanus spp., Haematopota spp., Philipomyia spp., Braula spp., Musca spp., Hydrotaea spp., Stomoxys spp., Haematobia spp., Morellia spp., Fannia spp., Glossina spp., Calliphora spp., Lucilia spp., Chrysomyia spp., Wohlfahrtia spp., Sarcophaga spp., Oestrus spp., Hypoderma spp., Gasterophilus spp., Hippobosca spp., Lipoptena spp. and Melophagus spp.

From the order of the Siphonapterida, for example, Pulex spp., Ctenocephalides spp., Xenopsylla spp. and Ceratophyllus spp.

From the order of the Heteropterida, for example, Cimex spp., Triatoma spp., Rhodnius spp. and Panstrongylus spp.

From the order of the Blattarida, for example, *Blatta orientalis, Periplaneta americana, Blattela germanica* and Supella spp.

From the sub-class of the Acaria (Acarida) and the orders of the Meta- and Mesostigmata, for example, Argas spp., Ornithodorus spp., Otobius spp., Ixodes spp., Amblyomma spp., Boophilus spp., Dermacentor spp., Haemaphysalis spp., Hyalomma spp., Rhipicephalus spp., Dermanyssus spp., Raillietia spp., Pneumonyssus spp., Sternostoma spp. and Varroa spp.

From the order of the Actinedida (Prostigmata) and Acaridida (Astigmata), for example, Acarapis spp., Cheyletiella spp., Ornithocheyletia spp., Myobia spp., Psorergates spp., Demodex spp., Trombicula spp., Listrophorus spp., Acarus spp., Tyrophagus spp., Caloglyphus spp., Hypodectes spp., Pterolichus spp., Psoroptes spp., Chorioptes spp., Otodectes spp., Sarcoptes spp., Notoedres spp., Knemidocoptes spp., Cytodites spp. and Laminosioptes spp.

The active compounds of the formula (I) according to the invention are also suitable for controlling arthropods which attack agricultural livestock, such as, for example, cattle, sheep, goats, horses, pigs, donkeys, camels, buffaloes, rabbits, chickens, turkeys, ducks, geese, honey bees, other domestic animals, such as, for example, dogs, cats, caged birds, aquarium fish, and so-called experimental animals, such as, for example, hamsters, guinea-pigs, rats and mice. By controlling these arthropods, it is intended to reduce deaths and decreased performances (in meat, milk, wool, hides, eggs, honey and the like), so that more economical and simpler animal keeping is made possible by using the active compounds according to the invention.

In the veterinary sector, the active compounds according to the invention are used in a known manner by enteral administration, for example in the form of tablets, capsules, drinks, drenches, granules, pastes, boluses, the feed-through method, suppositories, by parenteral administration, such as, for example, by means of injections (intramuscular, subcutaneous, intravenous, intraperitoneal and the like), implants, by nasal administration, by dermal administration, for example in the form of dipping or bathing, spraying, pouring-on and spotting-on, washing, dusting, and with the aid of shaped articles which comprise active compound, such as collars, ear tags, tail marks, limb bands, halters, marking devices and the like.

When administered to livestock, poultry, domestic animals and the like, the active compounds of the formula (I) can be used as formulations (for example powders, emulsions, flowables) which comprise the active compounds in an amount of 1 to 80%, either directly or after dilution by a factor of 100 to 10000, or they may be used in the form of a chemical bath.

Furthermore, it has been found that the compounds of the formula (I) according to the invention have a potent insecticidal action against insects which destroy industrial materials.

The following insects may be mentioned by way of example and as being preferred, but without any limitation:

Beetles, such as *Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis,* Xyleborus spec., Tryptodendron spec., *Apate monachus, Bostrychus capucins, Heterobostrychus brunneus,* Sinoxylon spec., *Dinoderus minutus.*

Dermapterans, such as *Sirex juvencus, Urocerus gigas, Urocerus gigas taignus, Urocerus augur.*

Termites, such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus.*

Bristletails, such as *Lepisma saccharina*.

Industrial materials are to be understood as meaning, in the present context, non-live materials, such as, preferably, synthetic materials, glues, sizes, paper and board, leather, wood and timber products, and paint.

The materials to be very particularly preferably protected against attack by insects are wood and timber products.

Wood and timber products which can be protected by the composition according to the invention or mixtures comprising such a composition are to be understood as meaning, for example, construction timber, wooden beams, railway sleepers, bridge components, jetties, wooden vehicles, boxes, pallets, containers, telephone poles, wood lagging, windows and doors made of wood, plywood, particle board, joiner's articles, or wood products which, quite generally, are used in the construction of houses or in joinery.

The active compounds can be used as such, in the form of concentrates or generally customary formulations, such as powders, granules, solutions, suspensions, emulsions or pastes.

The formulations mentioned can be prepared in a manner known per se, for example by mixing the active compounds with at least one solvent or diluent, emulsifier, dispersant and/or binder or fixative, water repellent, if appropriate desiccants and UV stabilizers and, if appropriate, colorants and pigments and other processing auxiliaries.

The insecticidal compositions or concentrates used for the protection of wood and wooden materials comprise the active compound according to the invention at a concentration of 0.0001 to 95% by weight, in particular 0.001 to 60% by weight.

The amount of the compositions or concentrates employed depends on the species and the occurrence of the insects and on the medium. The optimum rate of application can be determined upon use in each case by test series. However, in general, it suffices to employ 0.0001 to 20% by weight, preferably 0.001 to 10% by weight, of the active compound, based on the material to be protected.

The solvent and/or diluent used is an organochemical solvent or solvent mixture and/or an oily or oil-like organochemical solvent or solvent mixture of low volatility and/or a polar organochemical solvent or solvent mixture and/or water and, if appropriate, an emulsifier and/or wetting agent.

Organochemical solvents which are preferably employed are oily or oil-like solvents having an evaporation number of above 35 and a flashpoint of above 30° C., preferably above 45° C. Substances which are used as such oily and oil-like solvents which have low volatility and are insoluble in water are suitable mineral oils or their aromatic fractions, or mineral-oil-containing solvent mixtures, preferably white spirit, petroleum and/or alkylbenzene.

Substances which are advantageously used are mineral oils with a boiling range of 170 to 220° C., white spirit with a boiling range of 170 to 220° C., spindle oil with a boiling range of 250 to 350° C., petroleum or aromatics of boiling range 160 to 280° C., essence of terpentine and the like.

In a preferred embodiment, liquid aliphatic hydrocarbons with a boiling range of 180 to 210° C. or high-boiling mixtures of aromatic and aliphatic hydrocarbons with a boiling range of 180 to 220° C. and/or spindle oil and/or monochloronaphthalene, preferably α-monochloronaphthalene, are used.

The organic oily or oil-like solvents of low volatility having an evaporation number of above 35 and a flashpoint of above 30° C., preferably above 45° C., can be partially replaced by organochemical solvents of high or medium volatility, with the proviso that the solvent mixture also has an evaporation number of above 35 and a flashpoint of above 30° C., preferably above 45° C., and that the insecticide/fungicide mixture is soluble or emulsifiable in this solvent mixture.

In a preferred embodiment, part of the organochemical solvent or solvent mixture is replaced by an aliphatic polar organochemical solvent or solvent mixture. Substances which are preferably used are aliphatic organochemical solvents having hydroxyl and/or ester and/or ethers groups, such as, for example, glycol ether, esters and the like.

The organochemical binders used within the scope of the present invention are the synthetic resins and/or binding drying oils which are known per se and can be diluted with water and/or are soluble or dispersible or emulsifiable in the organo-chemical solvents employed, in particular binders composed of, or comprising, an acrylate resin, a vinyl resin, for example polyvinyl acetate, polyester resin, polycondensation or polyaddition resin, polyurethane resin, alkyd resin or modified alkyd resin, phenol resin, hydrocarbon resin, such as indene/coumarone resin, silicone resin, drying vegetable and/or drying oils and/or physically drying binders based on a natural and/or synthetic resin.

The synthetic resin used as the binder can be employed in the form of an emulsion, dispersion or solution. Up to 10% by weight of bitumen or bituminous substances can also be used as binders. In addition, colorants, pigments, water repellents, odour-masking substances and inhibitors or anti-corrosives known per se and the like can also be employed.

The composition or the concentrate preferably comprises, in accordance with the invention, at least one alkyd resin or modified alkyd resin and/or a drying vegetable oil as the organochemical binder. According to the invention, alkyd resins with an oil content of over 45% by weight, preferably 50 to 68% by weight.

All or some of the abovementioned binder can be replaced by a fixative (mixture) or a plasticizer (mixture). These additives are intended to prevent volatilization of the active compounds and crystallization or precipitation. They preferably replace 0.01 to 30% of the binder (based on 100% of binder employed).

The plasticizers are from the chemical classes of the phthalic esters, such as di-butyl phthalate, dioctyl phthalate or benzylbutyl phthalate, the phosphoric esters, such as tributyl phosphate, the adipic esters, such as di-(2-ethylhexyl) adipate, the stearates, such as butyl stearate or amyl stearate, the oleates, such as butyl oleate, the glycerol ethers or relatively high-molecular-weight glycol ethers, glycerol esters and p-toluenesulphonic esters.

Fixatives are chemically based on polyvinyl alkyl ethers, such as, for example, polyvinyl methyl ether, or ketones, such as benzophenone or ethylenebenzophenone.

Particularly suitable as a solvent or diluent is also water, if appropriate as a mixture with one or more of the abovementioned organochemical solvents or diluents, emulsifiers and dispersants.

Particularly effective protection of wood is achieved by large-scale industrial impregnation processes, for example vacuum, double-vacuum or pressure processes.

If appropriate, the ready-to-use compositions can additionally comprise other insecticides and, if appropriate, additionally one or more fungicides.

Suitable additional components which may be admixed are, preferably, the insecticides and fungicides mentioned in WO 94/29 268. The compounds mentioned in that document are expressly incorporated into the present application by reference.

Very particularly preferred components which may be admixed are insecticides, such as chlorpyrifos, phoxim, silafluofin, alphamethrin, cyfluthrin, cypermethrin, deltamethrin, permethrin, imidacloprid, NI-25, flufenoxuron, hexaflumuron and triflumuron, and fungicides, such as epoxyconazole, hexaconazole, azaconazole, propiconazole, tebuconazole, cyproconazole, metconazole, imazalil, dichlofluanid, tolylfluanid, 3-iodo-2-propinyl-butyl carbamate, N-octyl-isothiazolin-3-one and 4,5-dichloro-N-octylisothiazolin-3-one.

The preparation and the use of the active compounds according to the invention can be seen from the examples which follow.

PREPARATION EXAMPLES

Example 1

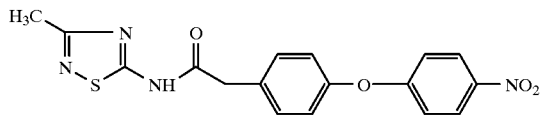

A solution of 6.10 g (0.0209 mol) of [4-(4-nitro)phenoxy]-phenylacetyl chloride in 20 ml of acetonitrile is added dropwise to a solution of 2.00 g (0.0174 mol) of 5-amino-3-methyl-1,2,4-thiadiazole and 1.50 g (0.0209 mol) of pyridine in 80 ml of acetonitrile. The mixture is stirred at 25° C. for 18 hours and then evaporated to dryness. The reaction mixture is taken up in water/ethyl acetate, and the organic phase is washed repeatedly with 10% strength aqueous sodium hydroxide solution.

After drying and concentrating, 3.2 g (44% of theory) of 3-methyl-5-[4-(4-nitro)phenoxy]phenylacetyl-amino-1,2,4-thiadiazole of melting point 168–170° C. are obtained.

Using a similar method or following the general preparation instructions, the following compounds of the formula (I) are obtained:

TABLE 1

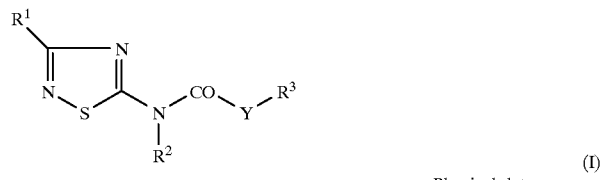

(I)

| Ex. No. | R¹ | R² | Y | R³ | Physical data ¹H—NMR (in D₆-DMSO, δ values referenced to TMS) |
|---|---|---|---|---|---|
| 2 | CH₃ | H | CH₂ | —⌬—O—⌬—CN | m.p. 126–28° C. |
| 3 | CH₃ | H | CH₂ | —⌬—O—⌬—OCF₃ | m.p. 80–81° C. |
| 4 | CH₃ | H | CH₂ | —⌬—O—⌬—SCF₃ | 2.41, 3.48, 7.06, 7.39, 7.72 |
| 5 | CH₃ | H | CH=CH | —⌬—O—⌬—NO₂ | 2.47, 6.56, 6.92, 7.22, 7.79, 8.27 |
| 6 | CH₃ | H | CH₂ | —⌬—CH₂O—⌬—Cl | 2.44, 3.78, 5.09, 6.98, 7.22, 7.46 |
| 7 | CH₃ | H | CH₂ | —⌬—CH₂O—⌬—NO₂ | 2.44, 3.79, 5.27, 6.98, 7.24, 7.72, 8.02 |
| 8 | CH₃ | H | CH₂ | —⌬—CH₂O—⌬—CN | 2.44, 3.79, 5.21, 6.97, 7.24, 7.85 |

TABLE 1-continued
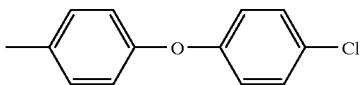
(I)
| Ex. No. | R¹ | R² | Y | R³ | Physical data ¹H—NMR (in D₆-DMSO, δ values referenced to TMS) |
|---|---|---|---|---|---|
| 9 | $CH_3$ | H | $CH_2$ | 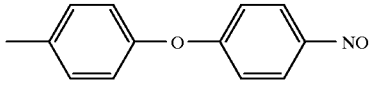 | 2.45, 3.87, 7.01, 7.25, 7.41 |
| 10 | $CH_3$ | H | $CH_2$—$CH_2$ |  | 2.44, 2.50, 2.99, 7.07, 7.35, 8.23 |
| 11 | 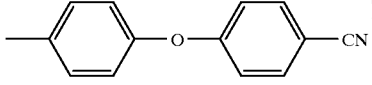 | H | $CH_2$ |  | 0.93, 2.16, 3.87, 7.07, 7.40, 7.82 |
| 12 | 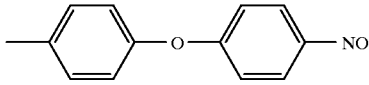 | H | $CH_2$ |  | 0.93, 2.16, 3.77, 7.10, 7.35, 8.23 |
| 13 | 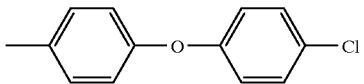 | H | $CH_2$ | 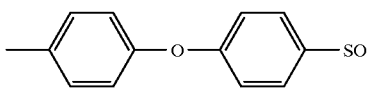 | 0.90, 2.12, 3.79, 7.00, 7.33, 7.40 |
| 14 | $CH_3$ | H | $CH_2$ |  | 2.43, 3.19, 3.88, 7.17, 7.41, 7.92 |
| 15 | 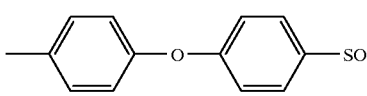 | H | $CH_2$ | 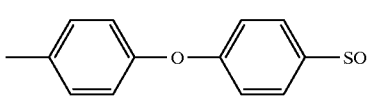 | 0.93, 2.13, 3.18, 2.87, 7.13, 7.42, |
| 16 | $C_2H_5$ | H | $CH_2$ | 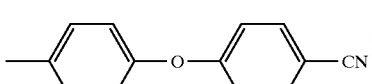 | 1.28, 2.80, 3.19, 7.12, 7.41, 7.89 |
| 17 | $C_2H_5$ | H | $CH_2$ | 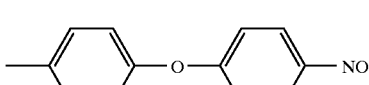 | 1.25, 2.79, 3.87, 7.07, 7.41, 7.83 |
| 18 | $C_2H_5$ | H | $CH_2$ |  | 1.26, 2.51, 3.84, 7.11, 7.45, 8.26 |

TABLE 1-continued
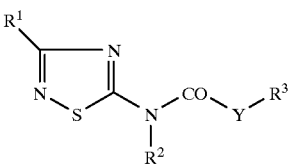
(I)
| Ex. No. | R¹ | R² | Y | R³ | Physical data ¹H—NMR (in D₆-DMSO, δ values referenced to TMS) |
|---|---|---|---|---|---|
| 19 | $C_2H_5$ | H | $CH_2$ | 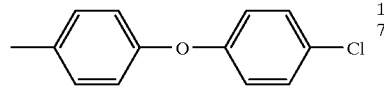 | 1.25, 2.50, 3.85, 7.00, 7.41 |
| 20 | $ClCH_2$ | H | $CH_2$ | 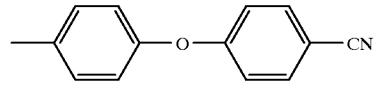 | 3.90, 4.78, 7.11, 7.44, 7.85 |
| 21 | $ClCH_2$ | H | $CH_2$ | 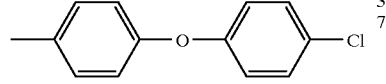 | 3.90, 4.77, 7.10, 7.45, 7.86 |
| 22 | 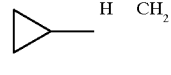 | H | $CH_2$ |  | |
| 23 | 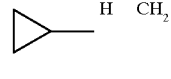 | H | $CH_2$ | 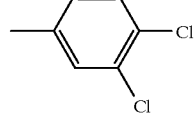 | |
| 24 | 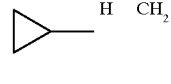 | H | $CH_2$ | 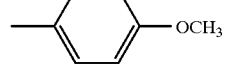 | m.p. 152° C. |
| 25 | $CH_3$ | H | $CH_2$ | 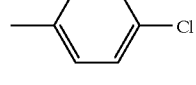 | m.p. 1523° C. |
| 26 | $CH_3$ | H | $CH_2$ | 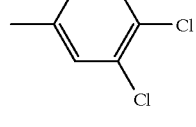 | m.p. 194° C. |
| 27 | $CH_3$ | H | $CH_2$ | 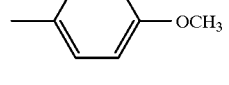 | |

TABLE 1-continued

(I)

| Ex. No. | R¹ | R² | Y | R³ | Physical data 1H—NMR (in D$_6$-DMSO, δ values referenced to TMS) |
|---|---|---|---|---|---|
| 28 | 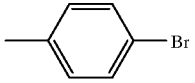 | H | CH$_2$ | ⟨benzene⟩—Br | m.p. 172° C. |

USE EXAMPLES

Example A

Phaedon Larvae Test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of the active compound of the desired concentration and are infested with mustard beetle larvae (*Phaedon cochleariae*) while the leaves are still moist.

After the specified period of time, the destruction in % is determined. 100% means that all the beetle larvae have been killed; 0% means that none of the beetle larvae have been killed.

In this test, a destruction of 100% was brought about, after 7 days, for example by the compounds of Preparation Examples 1, 2 and 3 at an exemplary active compound concentration of 0.1%.

Example B

Plutella Test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of the active compound of the desired concentration and are infested with caterpillars of the diamondback moth (*Plutella maculipennis*) while the leaves are still moist.

After the specified period of time, the destruction in % is determined. 100% means that all the caterpillars have been killed; 0% means that none of the caterpillars have been killed.

In this test, a destruction of 100% was brought about, after 7 days, for example by the compounds of Preparation Examples 1, 2 and 3 at an exemplary active compound concentration of 0.1%.

Example C

Spodoptera Frugiperda Test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of the active compound of the desired concentration and are infested with caterpillars of the owlet moth (*Spodoptera frugiperda*) while the leaves are still moist.

After the specified period of time, the destruction in % is determined. 100% means that all the caterpillars have been killed; 0% means that none of the caterpillars have been killed.

In this test, a destruction of 100% was brought about, after 7 days, for example by the compounds of Preparation Examples 1, 2 and 3 at an exemplary active compound concentration of 0.1%.

Example D

Nephotettix Test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Rice seedlings (*Oryzae sativa*) are treated by being dipped into the preparation of the active compound of the desired concentration and are infested with larvae of the green rice leafhopper (*Nephotettix cincticeps*) while the seedlings are still moist.

After the desired period of time, the destruction in % is determined. 100% means that all the leafhoppers have been killed; 0% means that none of the leafhoppers have been killed.

In this test, a destruction of 100% was brought about, after 6 days, for example by the compounds of Preparation Examples 1, 2 and 3 at an exemplary active compound concentration of 0.1%.

Example E

Myzus Test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Broad bean seedlings (*Vicia faba*) infested with aphids (*Myzus persicae*) are dipped into the preparation of the active compound of the desired concentration and placed into a plastic dish.

After the specified period of time, the destruction in % is determined. 100% means that all the aphids have been killed, 0% means that none of the aphids have been killed.

In this test, a destruction of at least 90% was brought about, after 6 days, for example by the compounds of Preparation Examples 1, 2 and 3 at an exemplary active compound concentration of 0.1%.

Example F
Tetranychus Test (OP resistant/dip treatment)
Solvent: 3 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with emulsifier-containing water to the desired concentration.

Bean plants (*Phaseolus vulgaris*) which are severely infested with all stages of the greenhouse red spider mite (*Tetranychus urticae*) are dipped into an active compound preparation of the desired concentration.

After the specified period of time, the action in % is determined. 100% means that all the spider mites have been killed; 0% means that none of the spider mites have been killed.

In this test, a destruction of 100% was achieved, after 13 days, for example by the compound of Preparation Example 3 at an exemplary active compound concentration of 0.1%.

Example G
Test With Boophilus Microplus Resistant/SP-resistant Parkhurst Strain
Test animals: adult females which have sucked themselves full
Solvent: dimethyl sulphoxide 20 mg of active compound are dissolved in 1 ml of dimethyl sulphoxide, lower concentrations are prepared by dilution with the same solvent.

The test is carried out in 5 replications. 1 µl of the solutions is injected into the abdomen and the animals are transferred into dishes and kept in a controlled-environment chamber. The activity is determined via the inhibition of oviposition. 100% means that no tick has deposited any eggs.

In this test, an activity of 100% was shown, for example, by the compound of Preparation Example 2 at an exemplary active compound concentration of 20 µg/animal.

Example H
Test with Fly Larvae/Development-inhibitory Action
Test animals: all larval stages of Lucilia cuprina (OP resistant) [pupae and adults (without contact with the active compound)]
Solvent: 35 parts by weight of ethylene glycol monomethyl ether
Emulsifier: 35 parts by weight of nonylphenol polyglycol ether To produce a suitable preparation, 3 parts by weight of active compound are mixed with 7 parts by weight of the abovementioned mixture, and the resulting emulsion concentrate is diluted with water to the desired concentration.

For each individual concentration, 30 to 50 larvae are introduced into a test tube which contains 1 cm³ of horse meat. 500 µl of the dilution to be tested are pipetted onto this horse meat. The test tubes are placed in plastic beakers whose bottom is covered with sea sand, and kept in a climatized room (26° C.±1.5° C., 70%±10% relative humidity). The activity is examined (larvicidal action) after 24 hours and 48 hours. After emergence of the larvae (about 72 h), the test tubes are removed and perforated plastic lids are fitted to the beakers. After 1.5 times the development time (hatching of the control flies), the hatched flies and the pupae/cocoons are counted.

The activity criterion is the incidence of death in treated larvae after 48 h (larvicidal effect), or the inhibition of the hatching of adults from pupae or the inhibition of pupa formation. The criterion for the in-vitro activity of a substance is the inhibition of the development of the flies, or a development standstill before the adult stage. 100% larvicidal action means that all the larvae have been killed after 48 hours. 100% development-inhibitory action means that no adult flies have hatched.

In this test, an activity of 100% was shown, for example, by the compounds of Preparation Examples 2 and 3 at an exemplary active compound concentration of 1000 ppm.

Example I
Pyricularia Test (rice)/Protective
Solvent: 2.5 parts by weight of acetone
Emulsifier: 0.06 parts by weight of alkylanyl polyglycol ether To produce a suitable preparation of active compound, 1 part by weight of active compound is mixed with the stated amount of solvent, and the concentrate is diluted with water and the stated amount of emulsifier to the desired concentration.

To test for protective activity, young rice plants are sprayed with the preparation of active compound until dripping wet. One day after the spray coating has dried on, the plants are inoculated with an aqueous spore suspension of *Pyricularia oryzae*. The plants are then placed in a greenhouse at 100% relative atmospheric humidity and 25° C.

Evaluation of the disease infestation is carried out 4 days after the inoculation.

In this test, an activity of at least 70% with respect to an untreated control was shown, at an exemplary active compound rate of 750 g/ha and after a period of action of one day, for example by the compounds of Preparation Examples 3, 4, 22 and 23, and, after a period of action of 4 days, by the compounds of Preparation Examples 1, 2, 3 and 26.

Example J
Plasmopara Test (vines)/Protective
Solvent: 47 parts by weight of acetone
Emulsifier: 3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous spore suspension of *Plasmopara viticola* and then remain in a humidity chamber at about 20° C. and 100% relative atmospheric humidity for 1 day. The plants are then placed in a greenhouse at about 21° C. and about 90% atmospheric humidity for 5 days. The plants are then moistened and placed in a humidity chamber for 1 day.

Evaluation is carried out 6 days after the inoculation.

An activity of 0% means that the degree of infestation in treated plants is equivalent to an untreated control; an activity of 100% means that the treated plants are not infested.

In this test, an activity of 100% at an examplary active compound rate of 100 g/ha was shown for example by the compound of Preparation Example 2.

Example K

Sphaerotheca Test (cucumber)/Protective

Solvent: 47 parts by weight of acetone

Emulsifier: 3 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous spore suspension of *Sphaerotheca fuliginea*. The plants are then placed in a greenhouse at about 23° C. and at a relative atmospheric humidity of about 70%.

Evaluation is carried out 10 days after the inoculation.

An activity of 0% means that the degree of infestation in treated plants is equivalent to an untreated control; an activity of 100% means that the treated plants are not infested.

In this test, an activity of 98% at an examplary active compound rate of 100 g/ha was shown for example by the compound of Preparation Example 2.

Example L

Uncinula Test (vines)/Protective

Solvent: 47 parts by weight of acetone

Emulsifier: 3 parts by weight of alkylaryl polyglycol

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous spore suspension of *Uncinula necator*.

The plants are then placed in a greenhouse at about 23° C. and at a relative atmospheric humidity of about 70%.

Evaluation is carried out 14 days after the inoculation.

An activity of 0% means that the degree of infestation in treated plants is equivalent to an untreated control; an activity of 100% means that the treated plants are not infested.

In this test, an activity of 100% at an examplary active compound rate of 100 g/ha was shown for example.

Example M

Venturia Test (apple)/Protective

Solvent: 47 parts by weight of acetone

Emulsifier: 3 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism (*Venturia inaequalis*) and then remain in an incubation cabin at 20° C. and 100% relative atmospheric humidity for 1 day.

The plants are then placed in a greenhouse at 21° C. and a relative atmospheric humidity of about 90%.

Evaluation is carried out 12 days after the inoculation.

An activity of 0% means that the degree of infestation in treated plants is equivalent to an untreated control; an activity of 100% means that the treated plants are not infested.

In this test, an activity of 94% at an examplary active compound rate of 100 g/ha was shown for example by the compound of Preparation Example 2.

We claim:

1. Compounds of the formula (I)

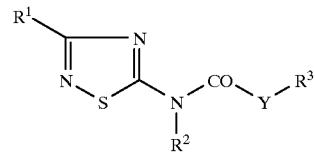

in which $R^1$ represents alkyl, halogenoalkyl, alkoxyalkyl, alkylthioalkyl, alkoxy, alkylthio or optionally substituted cycloalkyl, $R^2$ represents hydrogen, alkyl, halogenoalkyl, alkoxyalkyl, alkylcarbonyl, alkylsulphonyl, respectively optionally substituted arylcarbonyl, arylsulphonyl or arylalkyl or optionally substituted cycloalkyl, $R^3$ represents optionally substituted aryl, optionally substituted cycloalkyl or optionally substituted cycloalkenyl and Y represents optionally substituted alkylene, alkenylene or alkyleneoxy.

2. Compounds of the formula (I) according to claim 1 in which $R^1$ represents $C_1$–$C_4$-alkyl, $C_1$–$C_4$-halogenoalkyl having 1 to 5 identical or different halogen atoms, such as fluorine, chlorine and bromine atoms, $C_1$–$C_4$-alkoxy-$C_1$–$C_4$-alkyl, $C_1$–$C_4$-alkylthio-$C_1$–$C_4$-alkyl, $C_1$–$C_4$-alkoxy, $C_1$–$C_4$-alkylthio or $C_3$–$C_6$-cycloalkyl which is optionally mono- to trisubstituted by identical or different $C_1$–$C_4$-alkyl or halogen substituents, $R^2$ represents hydrogen, $C_1$–$C_4$-alkyl, $C_1$–$C_4$-halogenoalkyl having 1 to 5 identical or different halogen atoms, such as fluorine and chlorine atoms, $C_1$–$C_4$-alkoxy-$C_1$–$C_4$-alkyl, $C_1$–$C_4$-alkyl-carbonyl, $C_1$–$C_4$-alkylsulphonyl, phenylcarbonyl, phenylsulphonyl or benzyl, each of which is optionally mono- to trisubstituted on the phenyl ring by identical or different substituents from the group consisting of halogen, nitro, cyano, $C_1$–$C_4$-alkyl, $C_1$–$C_2$-halogenoalkyl having 1 to 5 identical or different halogen atoms, such as fluorine and chlorine atoms, $C_1$–$C_4$-alkoxy, $C_1$–$C_4$-alkylthio, $C_1$–$C_2$-halogenoalkoxy having 1 to 5 identical or different halogen atoms, such as fluorine and chlorine atoms, or $C_1$–$C_2$-halogenoalkylthio having 1 to 5 identical or different halogen atoms, such as fluorine and chlorine atoms, or represents $C_3$–$C_6$-cycloalkyl which is optionally mono- to trisubstituted by identical or different $C_1$–$C_4$-alkyl or halogen substituents, $R^3$ represents phenyl which is optionally mono- to trisubstituted by identical or different substituents from the group consisting of halogen, nitro, cyano, $C_1$–$C_{12}$- alkyl, $C_1$–$C_{12}$-halogenoalkyl having 1 to 5 identical or different halogen atoms, such as fluorine and chlorine atoms, $C_1$–$C_{12}$-alkoxy, $C_1$–$C_{12}$-halogenoalkoxy having 1 to 5 identical or different halogen atoms, such as fluorine and chlorine atoms, $C_1$–$C_{12}$-alkylthio, $C_1$–$C_{12}$-halogenoalkylthio having 1 to 5 identical or different halogen atoms, such as fluorine and chlorine atoms, $C_2$–$C_{12}$-alkenyl, $C_2$–$C_{12}$-halogenoalkenyl having 1 to 5 identical or different halogen atoms, such as fluorine and chlorine atoms, $C_3$–$C_8$-cycloalkyl which is optionally mono- to trisubstituted by identical or different $C_1$–$C_4$-alkyl or halogen substituents, and phenyl, phenoxy, phenylthio or benzyl, each of which is optionally mono- to trisubstituted by identical or different substituents from the group consisting of halogen, nitro, cyano, $C_1$–$C_4$-alkyl, $C_1$–$C_4$-halogenoalkyl having 1 to 5 identical or different halogen atoms, such as fluorine and chlorine atoms, $C_1$–$C_4$-alkoxy, $C_1$–$C_4$-halogenoalkoxy having 1 to 5 identical or different halogen atoms, such as fluorine and chlorine atoms, $C_1$–$C_4$-alkylthio, $C_1$–$C_4$-halogenoalkylthio having 1 to 5 identical or different halogen atoms, such as fluorine and chlorine atoms, $C_1$–$C_4$-alkylthio-$C_1$–$C_4$-alkyl, $C_1$–$C_4$-alkylsulphonyl, $C_1$–$C_4$-halogenoalkylsulphonyl having 1 to 5 identical or different halogen atoms, such as fluorine and chlorine atoms, and $C_1$–$C_4$-alkoxycarbonyl, or represents $C_3$–$C_8$-cycloalkyl or $C_5$–$C_8$-cycloalkenyl, each of which is optionally mono- to trisubstituted by identical or different substituents from the group consisting of $C_1$–$C_4$-alkyl, $C_1$–$C_4$-halogenoalkyl having 1 to 5 identical or different halogen atoms, such as fluorine and chlorine atoms, $C_1$–$C_4$-alkoxy, $C_1$–$C_4$-halogenoalkoxy having 1 to 5 identical or different halogen atoms, such as fluorine and chlorine atoms, $C_3$–$C_8$-cycloalkyl, and phenyl which is optionally mono- to trisubstituted by identical or different substituents from the group consisting of halogen, cyano, nitro, $C_1$–$C_4$-alkyl, $C_1$–$C_4$-halogenoalkyl having 1 to 5 identical or different halogen atoms, such as fluorine and chlorine atoms, $C_1$–$C_4$-alkoxy and $C_1$–$C_4$-halogenoalkoxy having 1 to 5 identical or different halogen atoms, such as fluorine and chlorine atoms, and Y represents $C_1$–$C_6$-alkylene, $C_1$–$C_6$-hydroxyalkylene, $C_1$–$C_4$-alkoxy-$C_1$–$C_6$-alkylene, $C_1$–$C_4$-alkylcarbonyloxy-$C_1$–$C_6$-alkylene, cyano-$C_1$–$C_6$-alkylene, $C_1$–$C_4$-halogenoalkylene having 1 to 5 identical or different halogen atoms, such as fluorine and chlorine atoms; or $C_3$–$C_6$-cycloalkyl-$C_1$–$C_4$-alkylene, $C_2$–$C_4$-alkenylene or $C_1$–$C_4$-alkyleneoxy, each of which is optionally mono- to trisubstituted by identical or different substituents from the group consisting of fluorine, chlorine and methyl.

3. Compounds of the formula (I) according to claim 1 in which $R^1$ represents methyl, ethyl, n- or i-propyl, n-, i-, s- or t-butyl; $CH_2F$, $CHF_2$, $CF_3$, $CH_2Cl$, $CH_2Br$, $CHClCH_3$; methoxy, ethoxy, methoxymethyl, ethoxymethyl; methylthiomethyl or cyclopropyl, $R^2$ represents hydrogen, methyl, ethyl, n- or i-propyl; methoxymethyl, ethoxymethyl, n-propoxymethyl, n-butoxymethyl; methylcarbonyl, methylsulphonyl; phenylcarbonyl or benzyl, each of which is optionally mono- or disubstituted by identical or different substituents from the group consisting of fluorine, chlorine, methyl and trifluoromethyl; or cyclopropyl, $R^3$ represents phenyl which is optionally mono- to trisubstituted by identical or different substituents from the group consisting of halogen, nitro, cyano, $C_1$–$C_{12}$-alkyl, $C_1$–$C_{12}$-halogenoalkyl having 1 to 5 identical or different halogen atoms, such as fluorine and chlorine atoms, $C_1$–$C_4$-alkoxy, $C_1$–$C_4$-halogenoalkoxy having 1 to 5 identical or different halogen atoms, such as fluorine and chlorine atoms, $C_1$–$C_4$-alkylthio, $C_1$–$C_4$-halogenoalkylthio having 1 to 5 identical or different halogen atoms, such as fluorine and chlorine atoms, $C_2$–$C_4$-alkenyl, $C_2$–$C_4$-halogenoalkenyl having 1 to 5 identical or different halogen atoms, such as fluorine and chlorine atoms, and phenoxy or phenylthio, each of which is optionally mono- to trisubstituted by identical or different substituents from the group consisting of halogen, nitro, cyano, $C_1$–$C_4$-alkyl, $C_1$–$C_4$-halogenoalkyl having 1 to 5 identical or different halogen atoms, such as fluorine and chlorine atoms, $C_1$–$C_4$-alkoxy, $C_1$–$C_4$-halogenoalkoxy having 1 to 5 identical or different halogen atoms, such as fluorine and chlorine atoms, $C_1$–$C_4$-alkylthio, $C_1$–$C_4$-halogenoalkylthio having 1 to 5 identical or different halogen atoms, such as fluorine and chlorine atoms, $C_1$–$C_4$-alkylthio-$C_1$–$C_4$-alkyl, $C_1$–$C_4$-alkylsulphonyl, $C_1$–$C_4$-halogenoalkylsulphonyl having 1 to 5 identical or different halogen atoms, such as fluorine and chlorine atoms, and $C_1$–$C_4$-alkoxy-carbonyl, and Y represents one of the groups —$CH_2$—, —$CH(CH_3)$—, —$CH(C_2H_5)$—, —$CH(n\text{-}C_3H_7)$—, —$CH(i\text{-}C_3H_7)$—, —$CH_2CH_2$—, —$CH(OH)$—, —$CH(OCH_3)$—, —$CH(O$—$CO$—$CCH_3)$—, —$CH(CN)$—, —$CHF$—, —$CHCl$—,

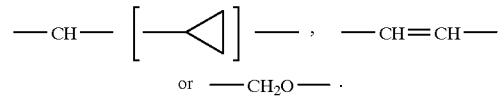

4. Compounds of the formula (I) according to claim 1 in which $R^1$ represents methyl, ethyl, n- or i-propyl, n-, i-, s- or t-butyl; $CH_2F$, $CHF_2$, $CF_3$, $CH_2Cl$, $CH_2Br$, methoxy, ethoxy or cyclopropyl, $R^2$ represents hydrogen, methyl, ethyl, methoxymethyl, ethoxymethyl, methylcarbonyl, phenylcarbonyl or methylsulphonyl, $R^3$ represents phenyl which is optionally mono- to trisubstituted by identical or different substituents from the group consisting of fluorine, chlorine, bromine, nitro, cyano, methyl, ethyl, n- or i-propyl, n-, i-, s- or t-butyl; methoxy, ethoxy, n- or i-propoxy, n-, i-, s- or t-butoxy; methylthio, $CF_3$, $OCF_3$, $OCHF_2$, $SCF_3$, $SCCl_2F$, $CH_2Br$, $CH_2Cl$, and phenoxy which is optionally mono- to trisubstituted by identical or different substituents from the group consisting of fluorine, chlorine, bromine, nitro, cyano, methyl, ethyl, n- or i-propyl, n-, i-, s- or t-butyl, methoxy, ethoxy, n- or i-propoxy, n-, i-, s- or t-butoxy, methylthio, methylthiomethyl, $CF_3$, $OCF_3$, $OCHF_2$, $SCF_3$, $SCCl_2F$, $CH_2Br$, $CH_2Cl$, methoxycarbonyl, methylsulphonyl and trifluoromethylsulphonyl, and Y represents —$CH_2$—, —$CH(CH_3)$—, —$CH_2CH_2$— or —$CH$=$CH$—.

5. A process for preparing compounds of the formula (I) according to claim 1, comprising reacting 5-amino-1,2,4-thiadiazoles of the formula (II)

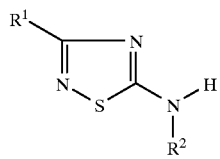
(II)

in which
R¹ and R² each have the meanings stated in claim 1 with acid halides of the formula (III)

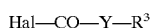
(III)

in which
R³ and Y each have the meanings stated in claim 1 and Hal represents halogen in the presence of a base and in the presence of a diluent.

6. Method for combating pests comprising applying a pesticidally effective amount of at least one compound of the formula (I) according to claim 1 to the pests or their habitat or to an area from which one desires to exclude such pests.

7. Process for preparing pesticides comprising mixing at least one compound of the formula (I) according to claim 1 with extenders and/or surface-active agents.

8. A pesticide comprising a pesticidally effective amount of at least one compound of the formula (I) according to claim 1 in combination with extenders and/or surface-active agents.

9. A pesticide comprising a pesticidally effective amount of at least one compound of the formula (I) according to claim 1 in combination with a diluent.

* * * * *